US005691287A

United States Patent [19]

Villars et al.

[11] Patent Number: 5,691,287

[45] Date of Patent: Nov. 25, 1997

[54] LOW IRRITATION CLEANSING BAR

[75] Inventors: William A. Villars, Racine; David H. Leifheit, Mount Pleasant, both of Wis.

[73] Assignee: S. C. Johnson & Son, Inc., Racine, Wis.

[21] Appl. No.: 576,654

[22] Filed: Dec. 21, 1995

[51] Int. Cl.[6] .................... C11D 7/48; C11D 9/48; C11D 10/04; A61K 7/50

[52] U.S. Cl. .................... 510/151; 510/130; 510/136; 510/155; 510/141

[58] Field of Search .................... 510/130, 136, 510/151, 139, 155, 156, 141

[56] References Cited

U.S. PATENT DOCUMENTS

| | | | |
|---|---|---|---|
| 3,671,634 | 6/1972 | Carlson et al. | 424/274 |
| 4,046,717 | 9/1977 | Johnston et al. | 252/546 |
| 4,100,097 | 7/1978 | O'Roark | 252/145 |
| 4,234,464 | 11/1980 | Morshauser | 252/544 |
| 4,278,570 | 7/1981 | Flom | 252/546 |
| 4,335,025 | 6/1982 | Barker et al. | 252/550 |
| 4,382,960 | 5/1983 | Flom | 424/358 |
| 4,495,079 | 1/1985 | Good | 252/106 |
| 4,707,293 | 11/1987 | Ferro | 252/174.17 |
| 4,774,016 | 9/1988 | Gazzani | 252/170 |
| 4,780,249 | 10/1988 | Pittz et al. | 252/547 |
| 4,790,956 | 12/1988 | Weipert et al. | 252/538 |
| 4,806,262 | 2/1989 | Synder | 252/90 |
| 4,808,322 | 2/1989 | McLaughlin | 252/121 |
| 4,892,729 | 1/1990 | Cavazza | 424/73 |
| 4,897,214 | 1/1990 | Gazzani | 252/170 |
| 4,919,837 | 4/1990 | Gluck | 252/106 |
| 4,941,990 | 7/1990 | McLaughlin | 252/121 |
| 4,966,754 | 10/1990 | Purohit et al. | 424/195.1 |
| 4,980,084 | 12/1990 | Vishnupad et al. | 252/309 |
| 5,047,177 | 9/1991 | Varco | 252/548 |
| 5,110,585 | 5/1992 | Chaudhuri et al. | 424/70 |
| 5,110,603 | 5/1992 | Rau | 424/466 |
| 5,132,037 | 7/1992 | Greene et al. | 252/108 |
| 5,208,013 | 5/1993 | Klein | 424/59 |
| 5,211,870 | 5/1993 | Gilbert et al. | 252/120 |
| 5,225,097 | 7/1993 | Kacher et al. | 252/112 |
| 5,225,098 | 7/1993 | Kacher et al. | 252/112 |
| 5,227,086 | 7/1993 | Kacher et al. | 252/112 |
| 5,262,079 | 11/1993 | Kacher et al. | 252/112 |
| 5,264,144 | 11/1993 | Moroney et al. | 252/117 |
| 5,264,145 | 11/1993 | French et al. | 252/117 |
| 5,294,363 | 3/1994 | Schwartz et al. | 252/108 |
| 5,372,751 | 12/1994 | Rys-Cicciari et al. | 252/554 |
| 5,389,279 | 2/1995 | Au et al. | 252/108 |
| 5,417,876 | 5/1995 | Tokosh et al. | 252/108 |
| 5,417,878 | 5/1995 | Takahata et al. | 252/174 |
| 5,425,892 | 6/1995 | Taneri et al. | 252/134 |
| 5,431,911 | 7/1995 | Reynolds | 424/401 |
| 5,441,663 | 8/1995 | Subramanyam et al. | 252/108 |
| 5,534,264 | 7/1996 | Fowler et al. | 424/489 |

FOREIGN PATENT DOCUMENTS

| | | |
|---|---|---|
| 8544564 | 1/1986 | Australia . |
| 0155888 | 8/1984 | European Pat. Off. . |
| 0158108 | 10/1985 | European Pat. Off. . |
| 0 186 453 | 2/1986 | European Pat. Off. . |
| 0249474 | 12/1987 | European Pat. Off. . |
| 1584830 | 1/1970 | France . |
| 63-179817 | 7/1988 | Japan . |
| 594165 | 5/1986 | U.S.S.R. . |
| 1570142 | 6/1980 | United Kingdom . |
| 2057486 | 4/1981 | United Kingdom . |
| 2262535 | 6/1993 | United Kingdom . |
| WO84/03622 | 9/1984 | WIPO . |
| WO86/02090 | 4/1986 | WIPO . |

OTHER PUBLICATIONS

Dove® Sensitive Skin Formula Beauty Bar wrapper ©1994 no month available.

*Primary Examiner*—Paul Lieberman
*Assistant Examiner*—Necholus Ogden

[57] ABSTRACT

A cleansing bar includes (a) from about 20% to about 35%, by weight of all ingredients in the cleansing bar, a synthetic detergent, sodium cocoyl isethionate, (b) from about 6% to about 11%, by weight of all ingredients in the cleansing bar, cetyl alcohol, wherein a mole to mole ratio of (a) to (b) is at least about 2.2:1, (c) at least about 30%, by weight of all ingredients in the cleansing bar, processed grain, (d) a buffer for adjusting the pH of the cleansing bar to be in a range from about 4.0 to about 5.5, and (e) from about 9% to about 20%, by weight of all ingredients in the cleansing bar, water. Also disclosed are methods of making such a cleansing bar.

32 Claims, No Drawings

LOW IRRITATION CLEANSING BAR

TECHNICAL FIELD

The present invention relates to the field of cleansing bars, more particularly to a soap-free cleansing bar substantially low in fatty acids, and even more particularly to a soap-free cleansing bar, substantially low in fatty acids, and including a synthetic detergent such as sodium cocoyl isethionate, a higher fatty alcohol such as cetyl alcohol, and a processed grain such as colloidal oatmeal.

BACKGROUND ART

Generally speaking, cleansing bars are personal care products which, upon the application of water, generate a cleansing lather to effect removal of dirt from a person's skin. One example of a cleansing bar is the traditional soap bar. The main cleaning ingredient in cleansing bars is known as "detergent." A detergent is defined as "a substance which reduces the surface tension of water, specifically a surface-active agent which concentrates at oil-water interfaces, exerts emulsifying action, and thus aids in removing soils." *Hawley's Condensed Chemical Dictionary,* 12th Ed., Van Nostrand Reinhold Co., New York (1993), p. 357. In other words, a detergent is a substance that cleans, particularly by helping to remove dirt. Detergents are themselves classified in the art as surface-active agents (also referred to as surfactants).

It is, of course, highly desirable that a cleansing bar be able to clean the skin effectively. Using a strong detergent affords effective cleaning of the skin. However, such a detergent may strip away some of the skin's natural oils. These oils protect the skin and retain moisture in and on the skin. Upon their removal, moisture loss from the skin increases, and the skin may become dry and irritated. The removal of natural oils, the accompanying increase in the loss of moisture from the skin, and the resulting heightening in dryness and irritation are primarily the adverse effects that a cleansing bar may have upon the skin. We hereinafter collectively refer to this as the "adverse effect on the skin" of a cleansing bar. We furthermore define a cleansing bar as being "mild", or low in irritation, if this adverse effect is low. We also define a cleansing bar as being milder than another, if it has less of the adverse effect on the skin.

Accordingly, it is highly desirable to provide a cleansing bar which cleans away dirt from the skin effectively, while being mild to the skin. It is not easy to fulfill both of these requirements. Some cleansing bars, namely those having soap as a detergent, fall short in this regard.

Soap cleans away dirt relatively well, but simply is not mild: instead, it can be harsh and irritate the skin. Soap is chemically defined in the art as a salt of a higher fatty acid with an alkali or a metal. *Grant and Hackh's Chemical Dictionary,* 5th Ed., McGraw-Hill, New York (1987), p. 535. A fatty acid, of course, is a carboxylic acid having an alkyl chain (with 4 to 22 carbon atoms) and a terminal carboxyl group —COOH. Id., p. 507. A higher fatty acid is defined as a fatty acid having about 12 to about 22 carbon atoms.

Although soap is relatively effective in removing dirt from the skin, it also can remove so much of the skin's natural oils that it can be harsh, irritating, and drying to the skin. Another disadvantage of soap is well known, namely the formation of soap rings or soap scum on surfaces. Soap rings or soap scum especially form in hard water. Although soap rings or soap scum typically form in a sink or bathtub, they may also develop, or be deposited, on the skin of an individual. Of course, formation of soap rings and soap scum is an undesirable characteristic for a cleansing bar. In view of the foregoing, it is desirable to have a cleansing bar which is soap-free.

Soap-free cleansing bars are known, and they typically include detergents other than soap, such as synthetic detergents. One widely-used group of synthetic detergents is the linear alkyl sulfonates. *Hawley's Condensed Chemical Dictionary,* supra, p. 357. Synthetic detergents are referred to in the art by the name "syndet." Cleansing bars which include synthetic detergents therefore are referred to as "syndet cleansing bars," or "syndet bars." Cleansing bars which include both soap and synthetic detergent are known as combination soap/synthetic detergent bars, or "combars."

Not only is it desirable to produce a soap-free cleansing bar, it is also desirable to have a cleansing bar which is substantially low in free fatty acids, because fatty acids may be converted into soap, which has the drawbacks discussed above. By "substantially low in free fatty acids" we mean that fatty acids are not specifically added as separate ingredients, but instead are present only in small amounts in the formulation of other ingredients. Conventionally, fatty acids are added to cleansing bars to provide binding. Such fatty acids are referred to in the art as free fatty acids. However, all such fatty acids are chemical relatives of soaps; they share almost identical chemical formulas, although fatty acids substitute a hydrogen atom for the alkali or metal of soaps. Fatty acids themselves can have adverse effects on the skin. Also, fatty acids can be converted to soaps. This conversion takes place especially at higher pHs, above about 7. Once fatty acids have been converted to soaps, they exhibit the disadvantages of soaps, as discussed above.

It is still further desirable, in our view, to have a cleansing bar which includes a processed grain such as colloidal oatmeal. That ingredient is commercially appealing to consumers, and can also serve as a skin protectant to retain moisture in the skin, thereby reducing the effect or impact on the skin of the cleansing bar.

It is still further desirable to have a cleansing bar which has a target pH of about 4.0 to about 5.5, and even more preferably from about 4.5 to about 5.1. The skin has a natural pH of about 4.5 to about 6.0. It is preferable to produce a cleansing bar having a pH at the lower end of the skin's range, namely, about 4.5 to about 5.1. This is because using a higher pH cleansing bar tends to raise the pH of the skin, which is undesirable because this can harm or damage the skin.

There have been attempts to produce a cleansing bar which addresses the foregoing goals; however, disadvantages exist. We tested a cleansing bar (hereinafter referred to as the "conventional oatmeal syndet cleansing bar"). This cleansing bar is a member of the subclass of cleansing bars known as "specialty" cleansing bars, which are known to be fairly mild. This bar was a soap-free syndet cleansing bar, and was low in free fatty acids. In addition, it included colloidal oatmeal, and had a pH within the skin range discussed above. However, our tests revealed that the conventional oatmeal syndet cleansing bar offered at least three areas for improvement:

(i) Mildness: Although the conventional oatmeal syndet cleansing bar was fairly mild, we sought to produce a cleansing bar having even less irritating or drying effect upon the skin as discussed above. The effect is especially important for people with abnormal skin or skin that easily becomes dry after washing.

(ii) Cracking: When the conventional oatmeal syndet cleansing bar was left to stand after being wetted during use, it tended to crack. This is because, in general, as a cleansing bar becomes wet, it expands, while as it becomes dry, it contracts. If the cleansing bar lacks enough internal binding and plasticity, then it tends to crack. This was true of the bar that we tested.

(iii) "Swamping:" The bar also tended to "swamp," which means that it absorbed so much water that it became soggy. The characteristics of swamping and cracking naturally are unacceptable to consumers.

SUMMARY OF THE INVENTION

Accordingly, a need has arisen to overcome drawbacks associated with conventional cleansing bars, and to provide a cleansing bar having properties desirable and acceptable to consumers.

One object of the present invention is to provide a cleansing bar which is milder than conventional cleansing bars, that is to say, it should have even less of an adverse effect on the skin, as discussed above.

Another object of the present invention is to provide such a cleansing bar which is soap-free and substantially low in free fatty acids.

An additional object of the present invention is to provide such a cleansing bar which includes an advantageous amount of processed grain.

Still another object of the present invention is to provide such a cleansing bar having a target pH of about 4.0 to about 5.5, and preferably about 4.5 to about 5.1.

Yet another object of the present invention is to provide such a cleansing bar that is less prone to structural and aesthetic problems such as cracking and swamping.

Still another object of the present invention is to provide methods of making cleansing bars having the desired properties of the present invention.

In another aspect, the present invention relates to a cleansing bar consisting essentially of (a) from about 20% to about 35%, by weight of all ingredients of the cleansing bar, of a synthetic detergent, sodium cocoyl isethionate; (b) from about 6% to about 11%, by weight of all ingredients of the cleansing bar, of cetyl alcohol, wherein a mole to mole ratio of (a) to (b) is at least about 2.2:1; (c) at least about 30%, by weight of all ingredients of the cleansing bar, of processed grain; (d) a buffer for adjusting the pH of the cleansing bar to be in a pH range from about 4.0 to about 5.5; and (e) from about 9% to about 20%, by weight of all ingredients of the cleansing bar, of water; (f) at least one of hardened vegetable shortening and hydrogenated vegetable oil, wherein the ingredients in (a) through (f) are combined into the cleansing bar.

In still another aspect, the present invention relates to a method of making a cleansing bar, the method comprising the steps of (a) mixing together glycerin, water, and preservatives; (b) mixing together processed grain and sodium cocoyl isethionate; (c) combining together the mixture formed in step (a) and the mixture formed in step (b); (d) adding cetyl alcohol to the mixture formed in step (c); (e) adjusting the pH of the mixture formed in step (d) by combining a buffer therewith; (f) extruding and pressing the mixture formed in step (e) to form a cleansing bar, wherein processed grain is present in an amount of at least about 30 wt % of all ingredients of the cleansing bar, sodium cocoyl isethionate in an amount of about 20 to about 35 wt % of all ingredients of the cleansing bar, cetyl alcohol in an amount of about 6 to about 11 wt % of all ingredients of the cleansing bar, and water in an amount of about 9 to about 20 wt % of all ingredients of the cleansing bar, and a mole to mole ratio of sodium cocoyl isethionate to cetyl alcohol is at least about 2.2:1.

In yet another aspect, the present invention relates to a method of making a cleansing bar, the method comprising the steps of: (a) mixing, while heating so as to melt, hardened vegetable shortening, hydrogenated vegetable oil, and cetyl alcohol; (b) mixing the mixture of step (a) together with sodium cocoyl isethionate; (c) mixing the mixture of step (b) together with processed grain; (d) adjusting the pH of the mixture of step (c) by combining a buffer therewith; (e) extruding and pressing the mixture formed in step (d) to form a cleansing bar, wherein, processed grain is present in an amount of at least about 30 wt % of all ingredients of the cleansing bar, sodium cocoyl isethionate in an amount of about 20 to about 35 wt % of all ingredients of the cleansing bar, cetyl alcohol in an amount of about 6 to about 11 wt % of all ingredients of the cleansing bar, and water in an amount of about 9 to about 14 wt % of all ingredients in the cleansing bar, and a mole to mole ratio of sodium cocoyl isethionate to cetyl alcohol is at least about 2.2:1.

The above-noted and other objects, advantages, and features of the present invention will become more apparent from the following description of the preferred embodiments.

BEST MODE FOR CARRYING OUT THE INVENTION

The preferred embodiments and the best mode for carrying out the invention will now be described.

A preferred embodiment of our invention is a cleansing bar that includes at least the following three ingredients: (i) the synthetic detergent, sodium cocoyl isethionate, (ii) the higher fatty alcohol, cetyl alcohol, and (iii) a processed grain. Our cleansing bar is preferably free of soap, and is substantially low in free fatty acids. Because our cleansing bar is soap-free and includes the synthetic detergent sodium cocoyl isethionate, it is a syndet cleansing bar.

Sodium cocoyl isethionate is an n-acyl isethionate salt having a molecular weight of approximately 338. It has the following formula:

$$R\overset{\overset{O}{\|}}{C}OCH_2CH_2SO_3^-Na^+,$$

where R is derived from coconut oil and has an alkyl chain distribution centered on $C_{12}$. We prefer to use sodium cocoyl isethionate from PPG Industries in a compound known by the tradename Jordapon CI-powder. Jordapon CI-powder has the following formulation: APHA-5% in 30% isopropyl alcohol solution (50% maximum), sodium cocoyl isethionate (80% minimum, molecular weight about 338), moisture (2% maximum), sodium chloride (0.8% maximum), and free fatty acid (8% maximum). As previously discussed, it is desirable that a cleansing bar be substantially low in free fatty acids. Although the Jordapon CI that we use does have some free fatty acids (8% maximum), the total amount of free fatty acid from the Jordapon CI in our cleansing bar is low (e.g., about 1.9 wt % to about 2.4 wt %), based on the amount of Jordapon CI that we prefer to use. Unless specified otherwise, all references to percent, wt %, or weight %, throughout the specification are to be interpreted as the percentage amount by weight with respect to all other ingredients of a composition.

Cetyl alcohol is a higher fatty alcohol having the formula $C_{16}H_{34}O$. We believe that cetyl alcohol from our cleansing bar is deposited on the skin during use, and plays a role in reducing the adverse effect of the cleansing bar on the skin.

Our cleansing bar also includes one or more processed grains. We define processed grain throughout this application to include, by way of example and not of limitation, powdered grain, defatted grain, grain starch, oil-extracted grain, bleached grain, soluble grain fiber, grain protein, grain hulls, grain kernels, and grain bran. Any suitable grain may be employed, including, for example, oat, wheat, rice, barley, and corn. Specific examples of these include colloidal oatmeal, oat flour, corn flour, oat starch, cornstarch, and defatted microporous oat fraction.

We prefer to include the processed grain, colloidal oatmeal, in our cleansing bar. Colloidal oatmeal is known in the field to be a skin protectant. A skin protectant is generally defined to be a barrier-like substance which helps prevent the skin from losing moisture. We also believe that colloidal oatmeal additionally may serve as a binder to help hold the cleansing bar together. In addition, colloidal oatmeal may act as an anti-itch agent (i.e., anti-pruritic). Accordingly, we prefer to include colloidal oatmeal in an amount of at least about 30% by weight of the total ingredients of the composition. We even more preferably include about 38 wt % colloidal oatmeal, as shown in our Examples, which are detailed below.

Based on our experience with colloidal oatmeal, we believe that it would be preferable to include at least about 30%, by weight of total ingredients, of processed grain in a cleansing bar in accordance with the present invention.

When combining together the sodium cocoyl isethionate, the processed grain, and the cetyl alcohol, we prefer to employ water as a formulation aid. Throughout the application, when we discuss water as an ingredient in the cleansing bar composition, we are referring to water as a separate ingredient, and not to water which, in bound or free form, is included in other ingredients.

In combination with the foregoing ingredients, our cleansing bar may include other, optional ingredients. The optional ingredients include (a) skin protectants, humectants, and moisturizers, (b) buffers, (c) foam enhancers, (d) preservatives, (e) whiteners, (f) thickeners, and (g) odor masking agents, for example. Of course, other, optional ingredients may be added, if desired, for other reasons, as long as the optional ingredients do not materially change the fundamental character (i.e., effective cleansing combined with advantageous mildness) of the cleansing bar.

The optional skin protectants, humectants, and moisturizers all play a role in preventing moisture loss away from the skin, and preferred examples include glycerin, PEG-14M, PEG-75, and occlusive moisturizers such as hardened vegetable shortening and hydrogenated vegetable oil.

Buffers are optionally employed to achieve the target pH range in the cleansing bar, and also help to resist a change in pH of the skin itself, when deposited on the skin during use of the cleansing bar. Preferred examples of buffers include sodium lactate, lactic acid, citric acid and sodium citrate. We vary their individual levels to achieve our target pH range.

Foam enhancers, which we optionally include, serve to increase the amount of foam or lather generated during use of the cleansing bar; we prefer to use Lauramide DEA, for example.

Preservatives, if desired, are included to prevent or inhibit bacterial or other microbial growth. Preferred examples include the antimicrobial substances isopropynyl butylcarbamate (hereinafter "IPBC") and sorbic acid.

Whiteners may be added to increase the whiteness of the cleansing bar. A preferred example is titanium dioxide.

Thickeners may be added as a formulation aid to make more solid the cleansing bar composition. Preferred thickeners include magnesium aluminum silicate.

Odor masking agents may also be added to reduce the odor of the cleansing bar. Preferred examples include benzaldehyde encapsulated in polyoxymethylene urea, and an odor masking agent identified as Y10249 including isopentylcyclohexanone, nopyl acetate, and camphylcyclohexanol.

In the preferred embodiment of the present invention, we set the ratio of sodium cocoyl isethionate to cetyl alcohol within a preferred range. This range was developed as follows.

During the course of our testing, we discovered that in some early samples of cleansing bars including sodium cocoyl isethionate, cetyl alcohol, and colloidal oatmeal, coarse crystals formed on the surface of the bar. Because these crystals would be unattractive to the consumer, we conducted experiments to determine their origin. We discovered that these crystals comprised cetyl alcohol, which had migrated to the surface. This type of phenomenon is scientifically referred to as "phase separation." In investigating the phase separation, we further discovered that, unexpectedly, there appeared to be a correlation between the formation of crystals and the ratio of the ingredients sodium cocoyl isethionate (hereinafter, "SCI") and cetyl alcohol (hereinafter, "CA") in our prototype cleansing bars. By ratio, we mean the mole to mole ratio (hereinafter, the "SCI:CA" ratio) of sodium cocoyl isethionate to cetyl alcohol, based on the ingredients of the cleansing bar taken as a whole. The SCI:CA ratio was calculated assuming molecular weights for cetyl alcohol of 242, and for sodium cocoyl isethionate of 338, and by multiplying the wt % ratio of the ingredients by the fraction 242/338, to obtain a mole to mole ratio, i.e.:

$$R1 = \left(\frac{\text{sodium cocoyl isethionate wt \%}}{\text{cetyl alcohol wt \%}}\right)\left(\frac{242}{338}\right) \quad (1)$$

In this ratio, wt % is defined as the percentage, by weight, of an ingredient with respect to the total weight of all ingredients of the composition.

We therefore performed a series of experiments to determine the effect of varying the ratio of SCI:CA. The results of our experiments, showing experimental prototype formulas of our cleansing bar, are detailed in the following Tables 1A through 1C where "v.light" is "very light," "v.low" is "very low," and "v.heavy" is "very heavy." We visually estimated the amount of crystal formation over time, and assigned rankings ranging from none to heavy based on our estimates.

TABLE 1A

Relative Component Levels in Formula By Weight %

| | FORMULA NO. | | | | | | |
|---|---|---|---|---|---|---|---|
| COMPONENT | 104 | 110 | 105 | 113 | 111 | 106 | 107 |
| SCI | low | low | medium | medium | high | high | high |
| Fats & Oils | high | high | low | low | high | low | low |
| Glycerin | high | low | high | Medium | high | low | medium |
| CA | high | high | high | high | high | high | low |
| SCI:CA (mole to mole) | 1.8 | 1.8 | 2.0 | 2.0 | 2.2 | 2.2 | 2.5 |

TABLE 1B

| Observation of CA Crystal Formation | | | | | | | |
|---|---|---|---|---|---|---|---|
| TIME, | FORMULA NO. | | | | | | |
| DAYS | 104 | 110 | 105 | 113 | 111 | 106 | 107 |
| 7 | | v. light | | none | none | | |
| 14 | Light | | v. light | | | none | none |
| 21 | | light | | light | none | | |
| 35 | heavy | | light | | | v. light | none |
| 54 | | heavy | | heavy | v. light | | |
| 68 | heavy | | heavy | | | v. light | none |

TABLE 1C

| Experimental Formulas By Weight % of All Ingredients in Formula | | | | | | | |
|---|---|---|---|---|---|---|---|
| | FORMULA NO. | | | | | | |
| COMPONENT | 104 | 110 | 105 | 113 | 111 | 106 | 107 |
| Sodium Cocoyl Isethionate | 20.0 | 20.0 | 23.0 | 23.0 | 25.0 | 25.3 | 25.3 |
| Cetyl Alcohol | 8.0 | 8.0 | 8.0 | 8.3 | 8.0 | 8.0 | 7.0 |
| Glycerin | 4.5 | 1.5 | 4.0 | 2.8 | 4.5 | 2.0 | 3.0 |
| Hydrogenated Vegetable Oil | 5.4 | 5.4 | 4.0 | 4.5 | 5.4 | 4.0 | 4.0 |
| Hardened Vegetable Shortening | 5.4 | 5.4 | 4.0 | 4.5 | 5.4 | 4.0 | 4.0 |
| Colloidal Oatmeal | 38.0 | 38.0 | 38.0 | 38.0 | 38.0 | 38.0 | |
| Lauramide DEA | 1.8 | 1.8 | 1.8 | 1.8 | 1.8 | 1.8 | 1.8 |
| PEG-75 | 2.8 | 2.8 | 2.8 | 2.8 | 2.8 | 2.8 | 2.8 |
| Lactic Acid, 80% | 1.5 | 1.5 | 1.5 | 1.5 | 1.5 | 1.5 | 1.5 |
| Sodium Lactate, 60% | 2.3 | 2.3 | 2.3 | 2.3 | 2.3 | 2.3 | 2.3 |
| Odor Masking Agents | 1.9 | 1.9 | 1.9 | 1.9 | 1.9 | 1.9 | 1.9 |
| Preservatives | 0.8 | 0.8 | 0.8 | 0.8 | 0.8 | 0.8 | 0.8 |
| Titanium Dioxide | 1.0 | 1.0 | 1.0 | 1.0 | 1.0 | 1.0 | 1.0 |
| Purified water | 6.6 | 9.6 | 8.0 | 7.1 | 1.6 | 6.6 | 6.6 |

Upon reviewing the data from our experiments, such as that in Tables 1A through 1C, we noticed that crystal formation was either very light or none for Samples 111, 106, and 107 (SCI:CA ratios of 2.2, 2.2, and 2.5, respectively). We also noticed that crystal formation reached levels of light or heavy for the remaining samples 104, 110, 105, and 113 (SCI:CA ratios of 1.8, 1.8, 2.0, and2.0, respectively). We therefore made a decision that our cleansing bar would preferably have an SCI:CA ratio of at least about 2.2. This level represented our judgment of a commercially acceptable level, at which crystal formation was substantially suppressed.

Accordingly, in the preferred embodiment of the present invention, the following condition is preferably met:

$$R1 \geqq \text{about } 2.2 \tag{2}$$

where R1 is defined in Equation (1).

We conducted additional experiments to see if our success vis-a-vis crystal formation with sodium cocoyl isethionate and cetyl alcohol could be carded over to other surfactants: it could not. In a first experiment, we substituted the surfactant sodium cocoyl diglycinate (hereinafter "SCD") for sodium cocoyl isethionate. Sodium cocoyl diglycinate has a molecular weight of about 426, and is represented by the following formula

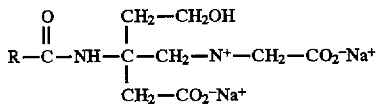

where R is derived from coconut oil with an alkyl chain distribution centered on $C_{12}$.

We used partial substitution of sodium cocoyl diglycinate for a mole equivalent amount of sodium cocoyl isethionate, rather than complete replacement, because sodium cocoyl diglycinate did not process well using our amalgamation and extrusion process for forming cleansing bars, which will be discussed in more detail below. In the experiment, we considered the total surfactant (SCI+SCD):CA (mole to mole) ratio. We prepared two samples having a ratio of 1.7, a level at which crystal growth was detected in the experiment of Tables 1A through 1C. We also prepared two samples having an (SCI+SCD):CA ratio of 2.2, a level at which crystal growth was substantially suppressed in previous experiments using the single surfactant sodium cocoyl isethionate. We adjusted pH upwards by omitting lactic acid and using triethanolamine to adjust to the final pH. We used visual observation to check for the presence of crystals. The results are detailed in Table 2 below.

TABLE 2

| Experimental Formulas for Sodium Cocoyl Diglycinate By Weight % of All Ingredients in Formula | | | | |
|---|---|---|---|---|
| | FORMULA NO. | | | |
| COMPONENT | 61A | 61B | 68A | 67A |
| Sodium Cocoyl Isethionate | 15.0 | 15.0 | 13.1 | 13.1 |
| Cetyl Alcohol | 8.0 | 8.0 | 7.0 | 7.0 |
| Sodium Cocoyl Diglycinate | 5.0 | 5.0 | 8.4 | 8.4 |
| Glycerin | 2.0 | 4.5 | 1.8 | 1.8 |
| Hydrogenated Vegetable Oil | 5.4 | 5.4 | 4.9 | 4.9 |
| Hardened Vegetable Shortening | 5.4 | 5.4 | 4.9 | 4.9 |
| Colloidal Oatmeal | 38.0 | 38.0 | 37.5 | 37.5 |
| Lauramide DEA | 1.8 | 1.8 | 1.6 | 1.6 |
| PEG-75 | 2.8 | 2.8 | 2.5 | 2.5 |
| Lactic Acid, 80% | 1.5 | 0 | 2.1 | 0 |
| Sodium Lactate, 60% | 2.3 | 2.3 | 0 | 2.1 |
| Odor Masking Agents | 1.9 | 1.9 | 1.8 | 1.8 |
| Preservatives | 0.8 | 0.8 | 0.8 | 0.8 |
| Titanium Dioxide | 1.0 | 1.0 | 1.0 | 1.0 |
| Purified water | 9.1 | 10.6 | 12.2 | 12.2 |
| pH, 5% in deionized water | 5.2 | 6.7 | 5.0 | 7.0 |
| Surfactant:Cetyl Alcohol, mole:mole | 1.7:1 | 1.7:1 | 2.2:1 | 2.2:1 |
| Crystal Formation/Days | | | | |
| 4 days | light | light | | |
| 5 days | | | light/moderate | none |
| 9 days | moderate | moderate | | |
| 14 days | | | moderate | none |
| 17 days | heavy | heavy | | |
| 27 days | | | heavy | none |

As can be seen from Table 2, suppression of crystals appeared only at the sample Formula No. 67A having a pH of 7.0 and a ratio of 2.2:1. This pH is, of course, outside our preferred target range. In the samples, Formula Nos. 68A and 61A, having a pH of 5.0 and 5.2, respectively, which are closer to our preferred target pH range, crystal formation was not suppressed. This demonstrates that the present invention provides advantageous crystal formation prevention which cannot be readily obtained by substitution of surfactants such as sodium cocoyl diglycinate.

Additional experiments confirmed the advantage of the present invention regarding alternative surfactants. We also tested partial replacement of sodium cocoyl isethionate with the surfactant sodium tallowyl glutamate. Sodium tallowyl glutamate (hereinafter "STG") is a surfactant having a molecular weight of about 355, and a structure as follows:

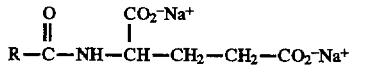

where R is derived from tallow with an alkyl chain distribution centered on $C_{18}$.

The results are detailed in the following Table 3.

TABLE 3

Experimental Formulas for Sodium Tallowyl Glutamate By Weight % of All Ingredients in Formula

| | FORMULA NO. | | | |
|---|---|---|---|---|
| COMPONENT | 114 | 145B | 68B | 67B |
| Sodium Cocoyl Isethionate | 15.0 | 15.0 | 13.1 | 13.1 |
| Cetyl Alcohol | 8.0 | 8.0 | 7.0 | 7.0 |
| Sodium Tallowyl Glutamate | 5.0 | 5.0 | 10.8 | 10.8 |
| Glycerin | 1.5 | 2.0 | 1.8 | 1.8 |
| Hydrogenated Vegetable Oil | 5.4 | 5.4 | 4.9 | 4.9 |
| Hardened Vegetable Shortening | 5.4 | 5.4 | 4.9 | 4.9 |
| Colloidal Oatmeal | 38.0 | 38.0 | 37.5 | 37.5 |
| Lauramide DEA | 1.8 | 1.8 | 1.6 | 1.6 |
| PEG-75 | 2.8 | 2.8 | 2.5 | 2.5 |
| Lactic Acid, 80% | 1.5 | 0 | 2.1 | 0 |
| Sodium Lactate, 60% | 2.3 | 2.3 | 0 | 2.1 |
| Odor Masking Agents | 1.9 | 1.9 | 1.8 | 1.8 |
| Preservatives | 0.8 | 0.8 | 0.8 | 0.8 |
| Titanium Dioxide | 1.0 | 1.0 | 1.0 | 1.0 |
| Purified water | 9.6 | 10.6 | 12.2 | 12.2 |
| pH, 5% in deionized water | 4.5 | 6.2 | 5.0 | 6.1 |
| Surfactant:Cetyl Alcohol, mole:mole | 1.7:1 | 1.7:1 | 2.2:1 | 2.2:1 |
| Crystal Formation/Days | | | | |
| 5 days | | | light/moderate | none |
| 7 days | heavy | | | |
| 14 days | | none | moderate | none |
| 21 days | v. heavy | | | |
| 27 days | | | heavy | none |
| 45 days | | none | | |

These results show that total surfactant (SCI+STG):CA ratios of 1.7:1 and 2.2:1 both stabilized the cleansing bar; however, this was at respective pHs of 6.2 and 6.1, both above our preferred pH range. This further demonstrates that the present invention provides advantageous crystal formation prevention which cannot be readily obtained from substitution of surfactants such as sodium tallowyl glutamate.

We have hypothesized that some of the improved performance may arise from the anionic (i.e., having a negative charge) nature of sodium cocoyl isethionate. In contrast, both sodium cocoyl diglycinate and sodium tallowyl glutamate are classified as amphoteric surfactants. Amphoteric means having the capacity of behaving either as an acid or a base. *Hawley's Condensed Chemical Dictionary,* supra, p. 72.

In amphoteric surfactants, such as sodium tallowyl glutamate, overall charge on a molecule of surfactant varies as a function of pH. For a high pH, there is very little charge on the nitrogen in sodium tallowyl glutamate, but complete ionization of the carboxylic acid group. Sodium tallowyl glutamate therefore generally acts anionic. However, at a lower pH, which matches the isoelectric point for the molecule of sodium tallowyl glutamate, the charge on the nitrogen is about equal to the charge on the carboxylic acid group. This yields an overall net charge of about 0. At an even lower pH, the cationic (+) charge on the nitrogen in sodium tallowyl glutamate increases, while the anionic charge (−) on the carboxylic acid group decreases (since it is being hydrogenated at a lower pH). Because amphoteric surfactants, such as sodium tallowyl glutamate, tend to exhibit increasing cationic character at lower pHs, such as the preferred target pHs of the present invention, they differ from sodium cocoyl isethionate, which, as discussed above, is anionic. This difference may be one of the factors causing the improved performance of sodium cocoyl isethionate in combination with cetyl alcohol and processed grains such as colloidal oatmeal, i.e., improved stability with suppression of crystal formation.

We have identified above a preferred lower SCI:CA ratio; however, as of yet, we have not identified a particular preferred upper limit on the SCI:CA ratio. Our Examples below show use of three different SCI:CA ratios, namely about 2.6, about 3.4, and about 2.2. Accordingly, one preferred range of SCI:CA which we know functions well would be about 2.2 to about 3.4.

As for preferred amounts of SCI and CA, we prefer to include from about 20 wt % to about 35 wt % of SCI. Our Examples below show that an even more preferred range of SCI is from about 23.60 wt % to about 32.25 wt %, i.e., approximately about 23 wt % to about 33 wt %. Furthermore, our Examples below show that a preferred range of cetyl alcohol is from about 6.70 wt % to about 8.45 wt %, i.e., approximately about 6 wt % to about 11 wt %.

As for water as an ingredient, Examples 1 and 2 below preferably employ about 13.30 wt % of water, while Example 3 employs about 9.38 wt % of water. During manufacturing of the cleansing bars, the amount of water, which is added as a formulation aid, may be adjusted to achieve a cleansing bar having a commercially acceptable consistency. In this regard, for Examples 1 and 2, we prefer to add 6 wt % or less of additional water as a formulation aid. That is to say, from about 13.30 wt % to about 13.30 wt %+6 wt %, i.e., from about 13.30 wt % to about 19.30 wt %, i.e., approximately 13 wt % to 20 wt %. As for Example 3, we prefer to add 4 wt % or less of additional water as a formulation aid. This yields a preferred range of from about 9.38 wt % to about 13.38 wt %, or approximately 9 wt % to 14 wt %. Overlapping these preferred ranges yields an overall preferred range of about 9 wt % to about 20 wt % for water as an ingredient.

EXAMPLES

Three examples of cleansing bar compositions in accordance with the present invention are set forth below.

In the list of ingredients for these examples, USP, FCC, and NF respectively refer to the standard reference books "U.S. Pharmacopeia", "Food and Chemicals Codex", and "National Formulary." Of course, this means that the ingredients so referenced are provided with standard uniform definitions.

Example 1

Cleansing Bar for Normal to Oily Skin

| Ingredients | Wt % |
|---|---|
| PEG-14M | 0.270 |
| purified water, USP | 13.300 |
| (an additional 6% (of total formula) or any smaller amount of purified water, USP may be added) | |
| glycerin, USP | 1.500 |
| potassium sorbate, FCC | 0.500 |
| colloidal oatmeal, USP | 38.000 |
| sodium cocoyl isethionate | 31.000 |
| titanium dioxide, USP | 0.850 |
| magnesium aluminum silicate, NF | 0.480 |
| lactic acid (88%, i.e., 88wt % lactic acid, 12 wt % water) | 1.700 |
| (Quantity of sodium lactate varied to obtain target pH) | |
| sodium lactate (60%, i.e., 60 wt % sodium lactate, 40 wt % water) | 1.900 |
| (Quantity of sodium lactate varied to obtain target pH) | |
| cetyl alcohol, NF | 8.450 |
| IPBC liquid | 0.300 |
| benzaldehyde, about 10% encapsulated in polyoxymethylene urea | 1.350 |
| odor masking agents (isopentylcyclohexanone, nopyl acetate, camphylcyclohexanol) | 0.400 |
| Total | 100.000 |

Example 1 shows the composition of a cleansing bar for normal-to-oily skin. This bar features an SCI:CA ratio of about 2.6. Example 1 also includes glycerin USP (moisturizer), sorbic acid FCC (antimicrobial), potassium sorbate (preservative), PEG-14M (moisturizer), titanium dioxide USP (whitener), lactic acid and sodium lactate (buffers for adjusting pH, as well as humectant-moisturizers), benzaldehyde and the above-listed odor masking agent (odor masking agents), IPBC liquid (antimicrobial preservative), purified water USP (a formulation aid to provide proper consistency), and magnesium aluminum silicate NF (a thickener).

Our preferred method for making the Example 1 cleansing bar is as follows. First, we prepared a cold premix, using a lightening mixer. We dispersed the PEG-14M in glycerin, and maintained agitation of the mixture until a creamy homogeneous liquid was formed. We then added purified water USP to a stainless steel mix tank. With the mixer of the stainless steel mix tank on, we slowly poured the PEG-14M/glycerin mixture from the lightening mixer into the water in the mix tank. We then added the IPBC solution, followed by the potassium sorbate, which was added with continuous mixing. We mixed the cold premix until it was uniform, prior to its first use (and maintained the mixing action to avoid separation of the mixture during use of the batch).

Once we prepared the cold premix, we combined the remaining ingredients in the following fashion, using a batch mixer. With the batch mixer off, we added in succession the processed grain, here colloidal oatmeal, sodium cocoyl isethionate, magnesium aluminum silicate, titanium dioxide, and encapsulated benzaldehyde. We then turned the mixer on, and mixed the above powders for about 2–3 minutes. With the mixer running, we added in succession the following pre-weighed materials: the cold premix discussed above, lactic acid, sodium lactate, purified water, and above-listed odor masking agent. We then stopped the mixer and added cetyl alcohol, which we had heated until it attained a melted state. After starting the mixer again, we mixed until the color was uniform, and the mixture attained a lumpy consistency. We then dropped the mixed batch into the feed hopper of a preliminary plodder, and extruded, pressed, and packaged the cleansing bars.

Before placing the batch in the plodder in this example, we adjusted the pH in the following fashion. We first calculated pH by preparing a 5% solution of a sample of the cleansing bar composition in deionized water. Next, we measured pH with a pH meter. Whenever we refer to pH of a cleansing bar in this application, we are referring to pH as measured by this method. To adjust the pH downward, we added additional lactic acid; to adjust the pH upward, we added additional sodium lactate. Thereby, we were able to produce a cleansing bar having a pH in our preferred target range of about 4.0 to about 5.5, even more preferably about 4.5 to about 5.1.

We used this pH adjustment method in the methods of making Examples 2 and 3 also.

Example 2

Cleansing Bar for Acne-Prone Skin

| Ingredients | Wt % |
|---|---|
| potassium sorbate, FCC | 0.500 |
| glycerin, USP 99.5% | 1.500 |
| PEG-14M | 0.270 |
| purified water, USP | 13.300 |
| (An additional 6% (of total formula) or smaller amount of purified water, USP may be added) | |
| colloidal oatmeal, USP | 38.000 |
| lactic acid (88%) | 1.700 |
| (Quantity of lactic acid varied to obtain target pH) | |
| sodium lactate (60%) | 1.900 |
| (Quantity of sodium lactate varied to obtain target pH) | |
| magnesium aluminum silicate | 0.480 |
| salicylic acid, USP, powder | 0.500 |
| sodium cocoyl isethionate | 32.250 |
| titanium dioxide | 0.850 |
| cetyl alcohol, NF | 6.700 |
| IPBC liquid | 0.300 |
| benzaldehyde, about 10% encapsulated | 1.350 |
| odor masking agents (isopentylcyclohexanone, nopyl acetate, camphylcyclohexanol) | 0.400 |
| Total | 100.000 |

Example 2 shows the composition of a cleansing bar for acne-prone skin. In general, acne-prone skin is oilier than normal skin; accordingly, this bar features the highest level, among the three examples, of surfactant: the SCI:CA ratio is about 3.4.

Our preferred method for making the Example 2 cleansing bar is as follows. Using the proportions of ingredients set forth above for Example 2, we used the basic method set forth above for Example 1, but we added salicylic acid in between adding the titanium dioxide and adding the encapsulated benzaldehyde.

Example 3

Cleansing Bar for Dry Skin

| Ingredient | Wt % |
|---|---|
| vegetable shortening hardened | 3.700 |
| vegetable oil hydrogenated | 3.700 |
| Lauramide DEA | 1.500 |
| glycerin USP, 99.5% | 2.500 |

-continued

| Ingredient | Wt % |
|---|---|
| sorbic acid, FCC | 0.500 |
| colloidal oatmeal, USP | 38.000 |
| sodium cocoyl isethionate | 23.600 |
| PEG-75 | 2.500 |
| titanium dioxide, USP | 0.950 |
| lactic acid (88%) | 1.400 |
| (Quantity of lactic acid varied to obtain target pH) | |
| sodium lactate 60% | 2.120 |
| (Quantity of sodium lactate varied to obtain target pH) | |
| cetyl alcohol, NF | 7.550 |
| benzaldehyde, about 10% encapsulated | 1.800 |
| odor masking agents (isopentylcyclohexanone, nopyl acetate, camphylcyclohexanol) | 0.500 |
| IPBC liquid | 0.300 |
| purified water, USP | 9.380 |
| (An additional 4% (of total formula) or smaller amount of purified water, USP may be added). | |
| Total | 100.000 |

Example 3 is a cleansing bar for dry skin. To provide relief for dry skin, this cleansing bar includes hardened vegetable shortening and hydrogenated vegetable oil, which serve as occlusive moisturizers. Among the three examples set forth herein, Example 3 also has the lowest SCI:CA ratio, namely about 2.2. The remaining ingredients are generally similar to those of Example 1, but include PEG-75 (moisturizer) and Lauramide DEA (foam enhancer).

Our preferred method for making the Example 3 cleansing bar is as follows. First, we prepared a hot premix. Using a steam-jacketed mix tank with an agitator, with the agitator off, we added hardened vegetable shortening to the tank. We then heated the tank to melt the hardened vegetable shortening. Next, we turned on the agitator and added the hydrogenated vegetable oil and the cetyl alcohol. We then maintained steam and agitation to completely melt the hydrogenated vegetable oil and hardened vegetable shortening. With the agitator running, we added in succession the following pre-weighed materials: glycerin, sorbic acid, and Lauramide DEA. We continued mixing for five minutes prior to the first use of the batch (and further continued mixing and maintaining the batch temperature, which was not to exceed 185° F., until the batch was entirely used).

Once we prepared the hot premix, we combined the remaining ingredients in the following fashion, using a mixer. With the mixer off, we added the hot premix, the IPBC liquid, and about half of the sodium cocoyl isethionate, and turned on the mixer to blend the mixture for about 1–2 minutes. With the mixer turned off again, we added in succession the following pre-weighed materials: the processed grain, here colloidal oatmeal, the remainder (i.e., the other half) of the sodium cocoyl isethionate, PEG-75, encapsulated benzaldehyde, and titanium dioxide. We turned the mixer back on, and mixed the combination for about 2–3 minutes. With the mixer running, we then added in succession the following pre-weighed materials: lactic acid, sodium lactate, purified water, and the above-listed odor masking agent. We mixed until the color was uniform, and the mixture attained a lumpy consistency. We then dropped the mixed batch into the feed hopper of the preliminary plodder, and extruded, pressed, and packaged the cleansing bars.

Comparative Testing

We performed tests of cleansing bars in accordance with the present invention, and found that they offered improved performance versus the conventional oatmeal syndet cleansing bars discussed above.

With respect to mildness, we performed tests and we found that cleaning bars in accordance with the present invention had less of an adverse effect on the skin (i.e., greater mildness) versus conventional oatmeal syndet cleansing bars. In the following tests excerpted below, we compared the irritating or drying effect of several cleansing bars on the skin.

TEST #1

We performed a forearm wash test in which we objectively determined the effect on the skin via TEWL measurement. TEWL is one of several quantifiable measures of mildness, and a high TEWL is not desirable. In particular, TEWL is a measure of the barrier function of the skin, which refers to the resistance of the skin to drying. Even more specifically, TEWL measures the amount of evaporation from the skin. If the amount of evaporation is great (high TEWL), then the barrier function of the skin is low, and the skin will become dry more rapidly. If the amount of evaporation is low (low TEWL), then the barrier function of the skin is high, and the skin will become dry less rapidly. Simply put, a cleansing bar which has a low effect on TEWL is a mild cleansing bar, i.e., one with little adverse effect on the skin. This, of course, is commercially desirable. The test showed that cleansing bars in accordance with the present invention had significantly less adverse effect on the skin than the conventional oatmeal syndet cleansing bars discussed above.

Test sites on the right and left forearms of subjects were washed twice a day for four consecutive days. An eighth site on each subject remained untreated (i.e., rinsed only with water) to act as a control. The test products are set forth below.

| Formula No. | Description |
|---|---|
| C | conventional oatmeal syndet cleansing bar 1 (colloidal oatmeal 51 wt % and SCI 22.5 wt %) |
| D | conventional oatmeal syndet cleansing bar 2 (colloidal oatmeal 51 wt % and SCI 24.5 wt %) |
| F | (colloidal oatmeal 38.00 wt %, SCI 32.25 wt %, CA 6.70 wt %, SCI:CA 3.4) |
| G | (colloidal oatmeal 38.00 wt %, SCI 31.00 wt %, CA 8.45 wt %, SCI:CA 2.5) |
| untreated | untreated (washed only with water) |

As can be seen, we tested two of the conventional oatmeal syndet cleansing bars (Samples C and D) together with two cleansing bars in accordance with the present invention (Samples F and G), the latter two having different SCI:CA ratios.

Skin condition on the test sites was measured instrumentally on Days 1 (baseline), 3 and 5. Instrumental measurements of TEWL were made using a ServoMed Evaporimeter. Measurements were taken prior to test washings on Days 1 and 3, and final measurements were taken on Day 5. Day 1 was considered the baseline.

The data is presented below in Table 4, where overall mean is calculated as the average of the Day 3 and Day 5 values.

TABLE 4

MEAN DIFFERENCES FROM BASELINE (TEWL)

| EVALUATION | FORMULA NO. C | D | F | G | Untreated |
|---|---|---|---|---|---|
| Day 3 | 1.69 | 1.50 | 1.26 | 1.15 | 0.96 |
| Day 5 | 1.84 | 2.04 | 1.64 | 1.43 | 0.69 |
| Overall Mean | 1.76 | 1.77 | 1.45 | 1.29 | 0.82 |

We analyzed the data using statistical analysis of variance (commonly abbreviated as ANOVA) techniques. Analysis of the ServoMed Evaporimeter TEWL readings indicated statistically significant differences in transepidermal water loss readings between the overall mean differences from baseline results for Samples D (1.77) and C (1.76), and Untreated (0.82) sites.

As can be seen from the foregoing, there was no significant statistical difference between either of Formulas F or G, and the untreated sites. This shows that cleansing bars prepared with Formulas F and G (i.e., in accordance with the present invention) were advantageously mild (had less adverse effect on the skin) versus the conventional oatmeal syndet cleansing bars.

TEST #2

A second test confirmed that cleansing bars in accordance with the present invention have less adverse effect on the skin than the conventional oatmeal syndet cleansing bars discussed above. This test was conducted in a manner similar to the first test, with cleansing bars as follows:

Sample A: colloidal oatmeal 38.00 wt %, SCI 23.60 wt %, CA 7.550 wt %;

Sample B: similar to sample D of Test #1;

Sample C: similar to sample C of Test #1;

Sample D: similar to sample G of Test #1; and

Sample E: similar to sample F of Test #1.

Samples A, D, and E were cleansing bars in accordance with the present invention, while samples B and C were conventional oatmeal syndet cleansing bars.

The results of the testing are detailed in Table 5 below.

TABLE 5

MEAN DIFFERENCES FROM BASELINE (TEWL)

| EVALUATION | FORMULA NO. A | B | C | D | E | Untreated |
|---|---|---|---|---|---|---|
| Day 3 | 2.95 | 4.29 | 4.26 | 3.34 | 4.64 | 2.17 |
| Day 5 | 2.51 | 4.20 | 3.97 | 3.11 | 3.55 | 0.99 |
| Overall Mean | 2.73 | 4.24 | 4.11 | 3.22 | 4.09 | 1.58 |

As can be seen, samples A, D, and E (respectively having overall mean TEWLs of 2.73, 3.22, and 4.09) have the lowest overall mean TEWLs of the cleansing bars tested. Our statistical analysis also showed that the differences between the overall mean TEWL of sample B (conventional) versus samples A or D, and of sample C (conventional) versus samples A or D, were statistically significant. Incidentally, we also tested a soap bar (TEWL 7.78), and another conventional specialty cleansing bar (TEWL 5.27). The results confirmed our findings that our cleansing bars were significantly improved with respect to mildness versus conventional cleansing bars and soap bars.

With respect to cracking and swamping, we tested a prototype cleansing bar according to the present invention including 41 wt % colloidal oatmeal, 34.5 wt % SCI, and 10.0% CA (SCI:CA ratio of about 2.4). We found no cracking in 10 of 10 bars tested, while 4 of 5 of the conventional oatmeal syndet cleansing bars suffered from cracking. The prototype cleansing bars in accordance with the present invention also exhibited greatly improved resistance to swamping, having a firmer feel after immersion in water for about 10 minutes. In contrast, the conventional oatmeal syndet cleansing bars discussed above became very slimy upon immersion. We believe that the synergistic combination of our ingredients including SCI, CA, and processed grain, helps to provide this improved performance.

While the present invention has been described with use of sodium cocoyl isethionate and cetyl alcohol as ingredients, other surfactants and fatty alcohols may be used in place of or in combination with those ingredients. For example, any other acylisethionate salt may be employed in place of or in combination with sodium cocoyl isethionate. Furthermore, other higher fatty alcohols, including, by way of example, myristyl alcohol and stearyl alcohol, may be employed in place of or in combination with cetyl alcohol. Of the higher fatty alcohols, we believe that cetyl, stearyl, and myristyl are preferable. Our experiments showed that stearyl alcohol (hereinafter "SA") also formed crystals at low SCI:SA ratios (more so at weight to weight (not mole to mole) ratios of 2.5:1, and less so at 3.6:1). Accordingly, it should be possible to replace some or all of the cetyl alcohol in our preferred embodiment with stearyl alcohol, where the fatty alcohol or alcohols are provided in an SCI:fatty alcohol ratio effective to substantially inhibit crystal formation. Other fatty alcohols could also or alternatively be used. However it should be noted that lauryl alcohol is often considered to be somewhat of an irritant. In the methods for making the cleansing bars, the foregoing alternative ingredients would be added in the manner specified for the compounds they replace in whole or in part.

INDUSTRIAL APPLICABILITY

The composition detailed above for use in the cleansing bar of the present invention may be used in many forms other than cleansing bars. For example, it is envisioned that the composition may instead be used in a semi-solid form such as a paste or cream, for example. Such a composition could be made by increasing the amount of water and lowering the amount of SCI, for example.

While the present invention has been described with respect to what are at present considered to be preferred embodiments, it is to be understood that the invention is not limited to the disclosed embodiments. To the contrary, the present invention is intended to cover various modifications and equivalent arrangements included within the spirit and scope of the appended claims. The following claims are to be accorded a broad interpretation, so as to encompass all such modifications and equivalent structures and functions.

What we claim is:

1. A cleansing bar consisting essentially of:

(a) from about 20% to about 35%, by weight of all ingredients of said cleansing bar, of a synthetic detergent, sodium cocoyl isethionate;

(b) from about 6% to about 11%, by weight of all ingredients of said cleansing bar, of cetyl alcohol, wherein a mole to mole ratio of (a) to (b) is at least about 2.2:1;

(c) at least about 30%, by weight of all ingredients of said cleansing bar, of processed grain;

(d) a buffer for adjusting the pH of said cleansing bar to be in a pH range from about 4.0 to about 5.5; and (e) from about 9% to about 20%, by weight of all ingredients of said cleansing bar, of water, wherein the ingredients in (a) through (e) are combined into said cleansing bar.

2. A cleansing bar according to claim 1, wherein said processed grain is selected from the group consisting of processed oat, processed wheat, and processed corn.

3. A cleansing bar according to claim 1, wherein said processed grain is selected from the group consisting of powdered grain, defatted grain, grain starch, oil-extracted grain, bleached grain, soluble grain fiber, grain protein, grain hulls, grain kernels, and bran.

4. A cleansing bar according to claim 3, wherein said processed grain is processed grain selected from the group consisting of oat, wheat, rice, barley, and corn.

5. A cleansing bar according to claim 1, wherein said processed grain is colloidal oatmeal.

6. A cleansing bar according to claim 5, wherein said colloidal oatmeal is present in an amount of about 38% by weight of all ingredients of said cleansing bar.

7. A cleansing bar according to claim 1, wherein said buffer comprises lactic acid and sodium lactate.

8. A cleansing bar according to claim 1, wherein the pH range of said cleansing bar is about 4.5 to about 5.1.

9. A cleansing bar according to claim 1, wherein the mole to mole ratio is less than or equal to about 3.4:1.

10. A cleansing bar according to claim 1, wherein said sodium cocoyl isethionate is present in an amount of from about 23% to about 35%, by weight of all ingredients of said cleansing bar.

11. A cleansing bar according to claim 1, wherein sodium cocoyl isethionate is present in an amount of about 31.00% by weight, and cetyl alcohol is present in an amount of about 8.45% by weight of all ingredients of said cleansing bar.

12. A cleansing bar according to claim 1, wherein sodium cocoyl isethionate is present in an amount of about 32.25% by weight, and cetyl alcohol is present in an amount of about 6.70% by weight of all ingredients of said cleansing bar.

13. A cleansing bar according to claim 1, wherein sodium cocoyl isethionate is present in an amount of about 23.60% by weight, and cetyl alcohol is present in an amount of about 7.55% by weight of all ingredients of said cleansing bar.

14. A cleansing bar consisting essentially of:

(a) from about 20% to about 35%, by weight of all ingredients of said cleansing bar, of a synthetic detergent, sodium cocoyl isethionate;

(b) from about 6% to about 11%, by weight of all ingredients of said cleansing bar, of cetyl alcohol, wherein a mole to mole ratio of (a) to (b) is at least about 2.2:1;

(c) at least about 30%, by weight of all ingredients of said cleansing bar, of processed grain;

(d) a buffer for adjusting the pH of said cleansing bar to be in a pH range from about 4.0 to about 5.5;

(e) from about 9% to about 20%, by weight of all ingredients of said cleansing bar, of water; and (f) at least one of hardened vegetable shortening and hydrogenated vegetable oil, wherein the ingredients in (a) through (f) are combined into said cleansing bar.

15. A method of making a cleansing bar, said method comprising the steps of:

(a) mixing together glycerin, water, and preservatives;

(b) mixing together processed grain and sodium cocoyl isethionate;

(c) combining together the mixture formed in step (a) and the mixture formed in step (b);

(d) adding cetyl alcohol to the mixture formed in step (c);

(e) adjusting the pH of the mixture formed in step (d) by combining a buffer therewith;

(f) extruding and pressing the mixture formed in step (e) to form a cleansing bar, wherein processed grain is present in an amount of at least about 30 wt % of all ingredients of the cleansing bar, sodium cocoyl isethionate in an amount of about 20 to about 35 wt % of all ingredients of the cleansing bar, cetyl alcohol in an amount of about 6 to about 11 wt % of all ingredients of the cleansing bar, and water in an amount of about 9 to about 20 wt % of all ingredients of the cleansing bar, and a mole to mole ratio of sodium cocoyl isethionate to cetyl alcohol is at least about 2.2:1.

16. A method according to claim 15, wherein the mole to mole ratio is less than or equal to about 3.4:1.

17. A method according to claim 15, wherein said adjusting step comprises the step of adjusting the pH to be about 4.0 to about 5.5 by using a buffer including lactic acid and sodium lactate.

18. A method according to claim 15, wherein the processed grain is selected from the group consisting of powdered grain, defatted grain, grain starch, oil-extracted grain, bleached grain, soluble grain fiber, grain protein, grain hulls, grain kernels, and grain bran.

19. A method according to claim 15, wherein the processed grain is selected from the group consisting of oat, wheat, and corn.

20. A method according to claim 15, wherein the processed grain comprises colloidal oatmeal.

21. A method according to claim 15, wherein the colloidal oatmeal is present in an amount of about 38% by weight of all ingredients of the cleansing bar.

22. A method of making a cleansing bar, said method comprising the steps of:

(a) mixing, while heating so as to melt, hardened vegetable shortening, hydrogenated vegetable oil, and cetyl alcohol;

(b) mixing the mixture of step (a) together with sodium cocoyl isethionate;

(c) mixing the mixture of step (b) together with processed grain;

(d) adjusting the pH of the mixture of step (c) by combining a buffer therewith;

(e) extruding and pressing the mixture formed in step (d) to form a cleansing bar, wherein, processed grain is present in an amount of at least about 30 wt % of all ingredients of the cleansing bar, sodium cocoyl isethionate in an amount of about 20 to about 35 wt % of all ingredients of the cleansing bar, cetyl alcohol in an amount of about 6 to about 11 wt % of all ingredients of the cleansing bar, and water in an amount of about 9 to about 14 wt % of all ingredients in the cleansing bar, and a mole to mole ratio of sodium cocoyl isethionate to cetyl alcohol is at least about 2.2:1.

23. A method according to claim 22, wherein the mole to mole ratio is less than or equal to about 3.4:1.

24. A method according to claim 22, wherein said adjusting step comprises the step of adjusting the pH to be about 4.0 to about 5.5 by using a buffer including lactic acid and sodium lactate.

25. A cleansing bar according to claim 22, wherein the processed grain is selected from the group consisting of powdered grain, defatted grain, grain starch, oil-extracted grain, bleached grain, soluble grain fiber, grain protein, grain hulls, grain kernels, and bran.

26. A cleansing bar according to claim 22, wherein the processed grain is selected from the group consisting of oat, wheat, rice, barley, and corn.

27. A method according to claim 22, wherein the processed grain comprises colloidal oatmeal.

28. A cleansing bar according to claim 27, wherein the colloidal oatmeal is present in an amount of about 38% by weight of all ingredients of the cleansing bar.

29. A cleansing bar according to claim 1, wherein said cleansing bar is soap-free.

30. A cleansing bar according to claim 14, wherein said cleansing bar is soap-free.

31. A method according to claim 15, wherein no step of adding free fatty acids to the cleansing bar is included in said method.

32. A method according to claim 22, wherein no step of adding free fatty acids to the cleansing bar is included in said method.

* * * * *